(12) United States Patent
Arad

(10) Patent No.: US 8,361,132 B2
(45) Date of Patent: Jan. 29, 2013

(54) SYSTEM AND METHOD FOR MANIPULATING A TEMPERATURE OF A PATIENT

(75) Inventor: Eliahu Arad, Tsofit (IL)

(73) Assignee: Biotempero Ltd., Zofit (IL)

( * ) Notice: Subject to any disclaimer, the term of this patent is extended or adjusted under 35 U.S.C. 154(b) by 311 days.

(21) Appl. No.: 12/651,490

(22) Filed: Jan. 4, 2010

(65) Prior Publication Data

US 2010/0198319 A1 Aug. 5, 2010

Related U.S. Application Data

(63) Continuation-in-part of application No. PCT/IL2008/000925, filed on Jul. 6, 2008.

(60) Provisional application No. 60/947,956, filed on Jul. 4, 2007, provisional application No. 60/983,196, filed on Oct. 28, 2007, provisional application No. 60/983,192, filed on Oct. 28, 2007, provisional application No. 60/985,362, filed on Nov. 5, 2007.

(51) Int. Cl.
*A61F 7/00* (2006.01)

(52) U.S. Cl. ............... 607/96; 607/104; 607/105
(58) Field of Classification Search .............. 607/104, 607/108, 109, 114
See application file for complete search history.

(56) References Cited

U.S. PATENT DOCUMENTS

| | | | | |
|---|---|---|---|---|
| 3,674,034 A | * | 7/1972 | Hardy | 607/104 |
| 4,306,566 A | * | 12/1981 | Sinko | 600/435 |
| 5,072,875 A | * | 12/1991 | Zacoi | 607/104 |
| 5,916,242 A | * | 6/1999 | Schwartz | 607/113 |
| 6,511,502 B2 | * | 1/2003 | Fletcher | 607/109 |
| 6,599,312 B2 | * | 7/2003 | Dobak, III | 607/105 |
| 7,189,253 B2 | * | 3/2007 | Lunderqvist et al. | 607/105 |
| 7,837,722 B2 | * | 11/2010 | Barbut et al. | 607/96 |

* cited by examiner

*Primary Examiner* — Roy Gibson
(74) *Attorney, Agent, or Firm* — Reches Patents

(57) ABSTRACT

A system for affecting a temperature of a patient, the system includes: a nose catheter that is adapted to be inserted into a nose upper channel and to receive a first fluid; and a temperature control and fluid supply unit that is adapted to supply the first fluid and control a temperature of the first fluid so as to affect a temperature of a brain of a patient when the nose catheter is inserted into the nose upper channel of a patient and receives the first fluid.

7 Claims, 14 Drawing Sheets

SYSTEM AND METHOD FOR MANIPULATING A TEMPERATURE OF A PATIENT

CROSS REFERENCE TO RELATED APPLICATIONS

This application is a Continuation In Part of a PCT international phase application Serial No. PCT/IL2008/000925, filed on Jul. 6, 2008 (and entitled SYSTEM AND METHOD FOR MANIPULATING A TEMPERATURE OF A PATIENT), that claims priority from the following U.S. provisional applications: application Ser. No. 60/947,956, filed on Jul. 4, 2007, application Ser. No. 60/983,196, filed on Oct. 28, 2007, application Ser. No. 60/983,192, filed on Oct. 28, 2007 and application Ser. No. 60/985,362, filed on Nov. 5, 2007, which are incorporated in their entirety herein by reference.

FIELD OF THE INVENTION

This disclosure relates generally to a system and method for manipulating a temperature of a patient.

BACKGROUND OF THE INVENTION

Brain damage following stoke and after successful cardiac resuscitation remains a major cause of morbidity and mortality worldwide. Stroke is the third cause of death in developed countries, ranking only behind cancer and heart disease. Over the last several years animal studies have demonstrated some brain protection by inducing mild brain cooling (32-35° C.). It has been shown that a reduction of the brain temperature by as little as 2° C. may substantially reduce the ischemic damage of the brain. Clinical trails in different patient's populations resulted in conflicting results. In both adults and children that were treated with hypothermia following major traumatic brain injuries there was no evidence of benefit outcome at 6 and 12 months after the injury. On the other hand hypothermia therapy was found to be of benefit in adults and newborns with a hypoxic-ischemic (leak of oxygen and blood supply to the brain) brain injury.

The treating physician has to apply an effective hypothermic therapy as soon as possible, and minimize the neurological injury. There are several approaches to induce hypothermia both invasive and non-invasive. Most of the currently published clinical studies used non-invasive external cooling approach. One approach is to cool the entire body inducing whole body hypothermia. The major drawbacks of this approach are the 1. slow cooling rate due to the large volume of the body 2. The cumbersome of the large devices that were used 3. The possible deleterious systemic effects such as metabolic, cardiovascular, pulmonary, coagulation and immunologic complications. These effects may occur during the hypothermia period as well as during the rewarming time. The increased risk of systemic complications when using whole body hypothermia may outweigh the brain protective benefits of such therapy.

Since the human brain weigh is only 2% of the total body weight and it receives 20% of the resting cardiac output it is not necessary to cool the entire body in order to achieve a reduction of the brain temperature. Presently brain cooling devices include surface cooling with ice-packs or cooling helmets and invasive approaches such as naso-phyrayngeal cooling and intra-carotid cold flushes. The cooling time while using these modalities is short (less than 1 h), however it provides more preferential cooling of the superficial areas of the brain that are in adjacent to the cooling device.

SUMMARY OF THE PRESENT INVENTION

The present invention provides a method and a device as described in the accompanying claims. Specific embodiments of the invention are set forth in the dependent claims. These and other aspects of the invention will be apparent from and elucidated with reference to the embodiments described hereinafter.

Conveniently, a system is provided and it can affect a temperature of a patient. The system includes: (i) a nose catheter that is adapted to be inserted into a nose upper channel and to receive a first fluid; and (ii) a temperature control and fluid supply unit that is adapted to supply the first fluid and control a temperature of the first fluid so as to affect a temperature of a brain of a patient when the nose catheter is inserted into the nose upper channel of a patient and receives the first fluid.

Conveniently, the temperature control and fluid supply unit is adapted to supply the first fluid and control the temperature of the first fluid so as to cool the brain of a patient when the nose catheter is inserted into the nose upper channel of a patient and receives the first fluid.

Conveniently, the system includes a temperature sensor adapted to sense a temperature of an organ of the patent; wherein the temperature control and fluid supply unit is adapted to determine a temperature of the first fluid in response to a temperature sensed by the temperature sensor.

Conveniently, the system further includes a stomach catheter that is adapted to be inserted into a stomach of the patient and to receive a second fluid; and wherein the temperature control and fluid supply unit is further adapted to supply the second fluid and control a temperature of the second fluid so as to affect a temperature of at least one organ that differs from the brain of the patient when the stomach catheter is inserted into the nose upper channel of the patient and receives the second fluid.

Conveniently, the temperature control and fluid supply unit is adapted to control temperatures of the first and second fluids so that during at least one period of time, the temperature of the first fluid differs from the temperature of the second fluid.

Conveniently, the temperature control and fluid supply unit is adapted to control temperatures of the first and second fluids so that during at least one other period of time, the temperature of the first fluid substantially equals the temperature of the second fluid.

Conveniently, the temperature control and fluid supply unit is adapted to control temperatures of the first and second fluids so that during a first period of time, the stomach catheter and the nasal catheter cool organs of the patient and during a second period of time that followed the first period of time the nasal catheter cools the brain of the patient while the stomach catheter warms at least one other organ of the patient.

Conveniently, the system further includes a carotid scarf that is adapted to be surround a neck of the patient and to receive a third fluid; and wherein the temperature control and fluid supply unit is further adapted to supply the third fluid and control a temperature of the second fluid so as to affect a temperature the brain of the patient when the stomach catheter is inserted into the nose upper channel of the patient and receives the second fluid.

Conveniently, the system further includes a stomach catheter that is adapted to be inserted into a stomach of the patient and to receive a second fluid; and wherein the temperature control and fluid supply unit is further adapted to supply the second fluid and control a temperature of the second fluid so as to affect a temperature of at least one organ that differs from the brain of the patient when the stomach catheter is inserted into the nose upper channel of the patient and receives the second fluid.

Conveniently, the system wherein the nasal catheter includes a stainless steel tip that receives the first fluid through an inlet and outputs the first fluid through an outlet.

A method for affecting a temperature of a patient, is provided. It includes: inserting a nose catheter into a nose upper channel of a patient; and supplying a first fluid to the nose catheter, by a temperature control and fluid supply unit, so as to affect a temperature of a brain of a patient.

Conveniently, the method includes supplying the first fluid to the nose catheter so as to cool the brain of the patient.

Conveniently, the method further includes: inserting a temperature sensor to the patient; sensing a temperature an organ of the patent, by the temperature sensor; and determining the temperature of the first fluid in response to temperature sensed by the temperature sensor.

Conveniently, the method further includes inserting a stomach catheter into a stomach of the patient; and supplying a second fluid to the stomach catheter so as to affect a temperature of at least one organ that differs from the brain of the patient.

Conveniently, the method includes controlling temperatures of the first and second fluids so that during at least one period of time, the temperature of the first fluid differs from the temperature of the second fluid. Conveniently, the method includes controlling temperatures of the first and second fluids so that during at least one other period of time, the temperature of the first fluid substantially equals the temperature of the second fluid.

Conveniently, the method includes controlling temperatures of the first and second fluids so that during a first period of time, the stomach catheter and the nasal catheter cool organs of the patient and during a second period of time that followed the first period of time the nasal catheter cools the brain of the patient while the stomach catheter warms at least one other organ of the patient.

Conveniently, the method further includes placing a carotid scarf around a neck of the patient; and supplying a third fluid to the carotid scarf, by a temperature control and fluid supply unit, so as to affect a temperature of a brain of a patient.

Conveniently, the method further includes inserting a stomach catheter into a stomach of the patient; and supplying a second fluid to the stomach catheter so as to affect a temperature of at least one organ that differs from the brain of the patient.

Conveniently, the method further includes inserting a stainless steel tip of the nasal catheter into the nose upper channel, providing the stainless steel tip first fluid via an inlet and draining the first fluid from the stainless steel tip through an outlet.

BRIEF DESCRIPTION OF THE DRAWINGS

Further details, aspects, and embodiments of the invention will be described, by way of example only, with reference to the drawings.

DETAILED DESCRIPTION OF THE DRAWINGS

Figure 1:
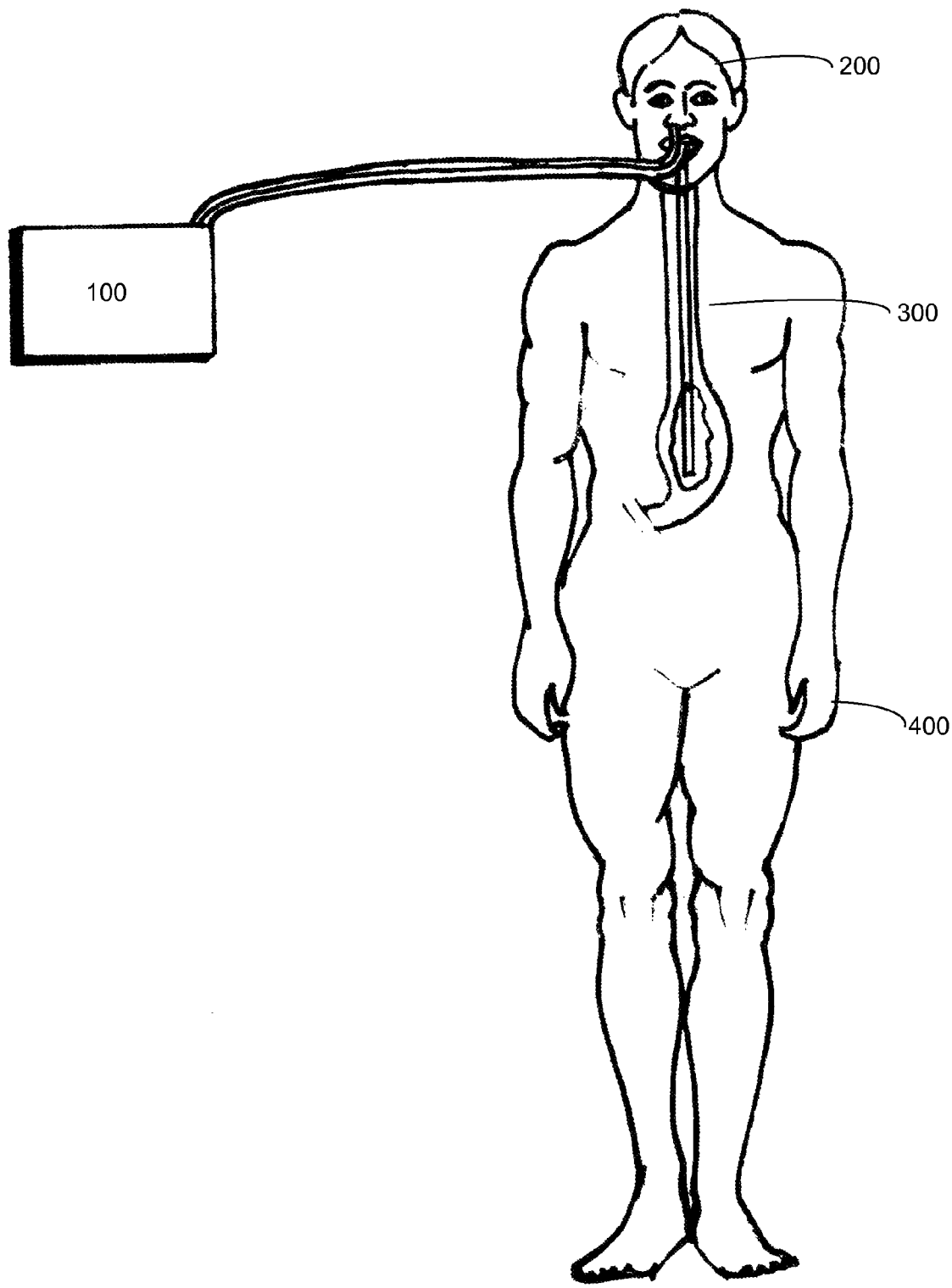
FIG. 1 schematically shows a patient, a temperature control and fluid supply unit, a stomach catheter, and a nose catheter according to an embodiment of the invention.

In the following specification, the invention will be described with reference to specific examples of embodiments of the invention. It will, however, be evident that various modifications and changes may be made therein without departing from the broader spirit and scope of the invention as set forth in the appended claims.

Because the apparatus implementing the present invention is, for the most part, composed of electronic components and circuits known to those skilled in the art, circuit details will not be explained in any greater extent than that considered necessary as illustrated above, for the understanding and appreciation of the underlying concepts of the present invention and in order not to obfuscate or distract from the teachings of the present invention.

It has been shown that cooling the brain using a nasal catheter is highly beneficial.

It has been shown that using two independently controllable temperature affecting elements can be used to cool the brain while heating other organs. Conveniently, multiple temperature affecting elements can first cool the patient and after a predefined time (of after reaching a certain temperature) the brain can be maintained at a low temperature by a temperature affecting element (such as a carotid scarf, and additionally or alternatively, a nasal catheter) while another temperature effecting element (such as a stomach catheter) warms other organs of the patient.

Conveniently, the system provides an advanced non-invasive temperature management solution, in the field of medical treatments. This system helps to control body temperature free of time pressure. The system provides controlled temperature management which allows continuous closed loop feedback and adjustment, based on the individual's physiological responses over a prolonged period.

Conveniently, the system can be applied for brain cooling therapy, as well as for treating cardiac arrest, acute stroke, traumatic brain injury, acute myocardial infraction and sepsis.

The system can include one or more temperature sensors, each can be included within or otherwise inserted in proximity to each temperature affecting element.

The system uses a fluid based temperature control mechanism in which fluids can be heater of cooled to desired temperature and then be sent through each temperature affecting element. Conveniently, a temperature sensor can include a naso-gastric tube is inserted through the nose, past the throat and reaches the stomach.

Any of the mentioned above temperature sensors can sense the temperature at different locations of the patient. If, for example, the sensed temperature falls the device can provide heat to the stomach and prevent the possible deleterious effects of total body hypothermia.

The system is small, portable and easily applied and therefore can by used by paramedics immediately even before arrival to the hospital. Applying brain cooling as soon as possible may future improve the neurological outcome. Since the system is portable, therapy can be applied during transfer both before arrival to the hospital but also during transport in the hospital itself between the different departments i.e. ER, radiology, ICU or the operating room.

The system can cool the scalp via a helmet, to the neck using a cooling collar and to the nasal area. By cooling different areas of the head and neck the brain temperature can be lowered quickly and evenly.

Nose Catheter

The nose catheter can be a non-invasive single use (disposable) catheter that is inserted into the nose upper channel of a patient.

Figure 2:
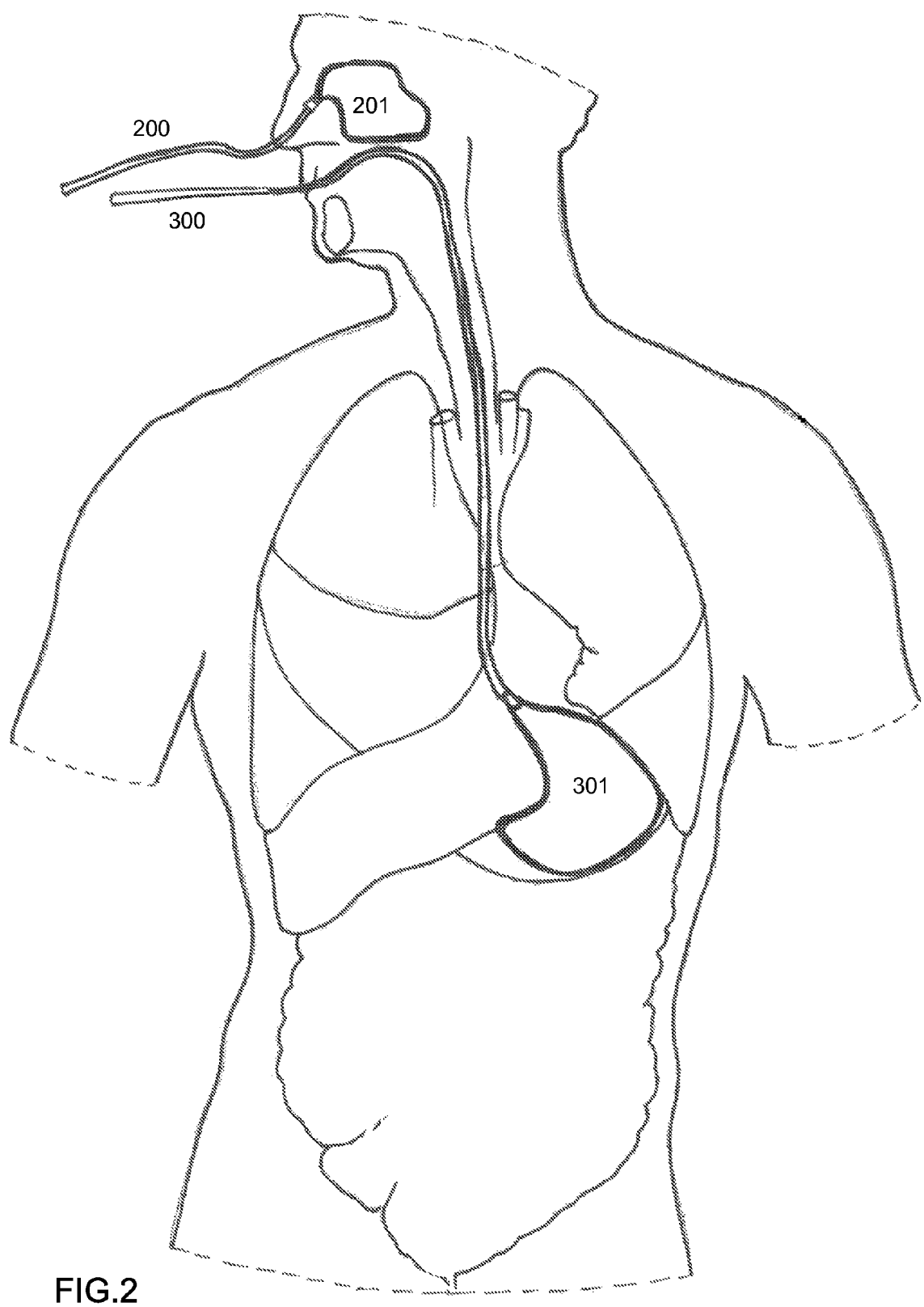
FIG. 2 is a cross sectional view of a patient, a stomach catheter, a nose catheter and areas proximate to each catheter that are directly affected by the temperature of the fluids that flows through each catheter according to an embodiment of the invention.
Figure 3:
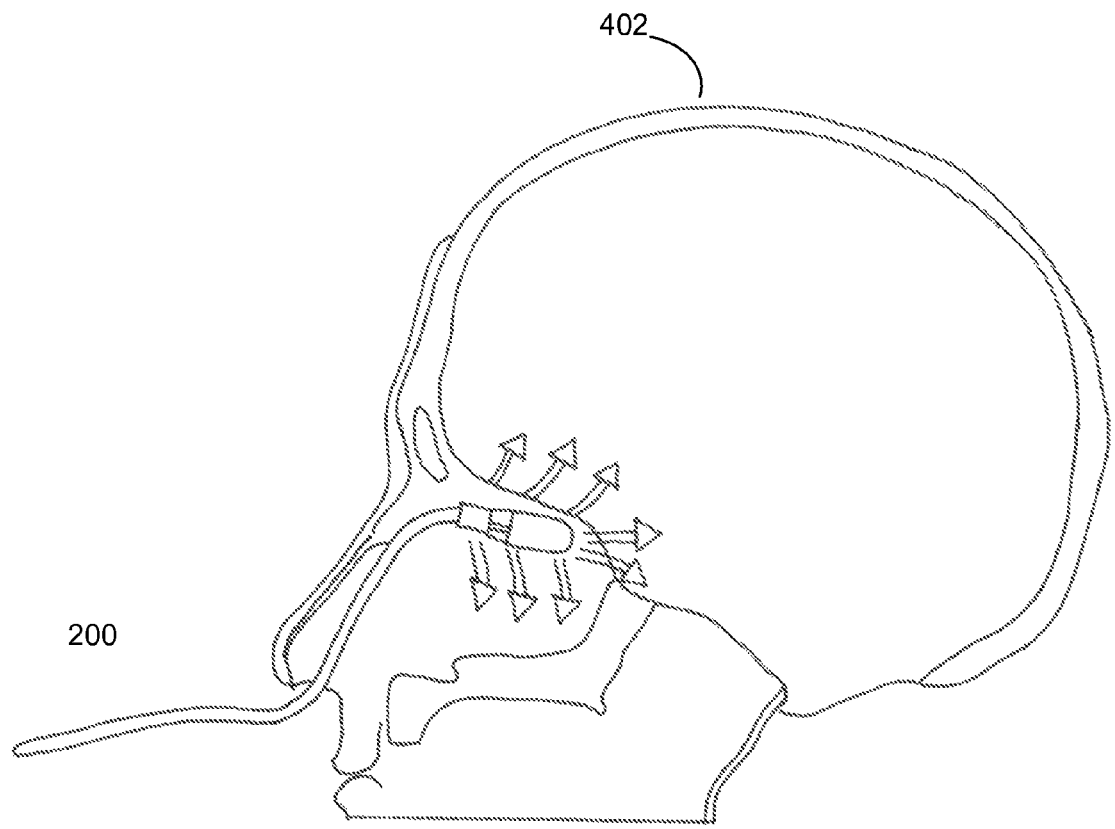
FIG. 3 is a cross sectional view of a skull of the patient and a nose catheter according to an embodiment of the invention.

FIG. 1 illustrates nose catheter 200 that is connected to temperature control and fluid supply unit 100. FIG. 2 illustrates the nose catheter 200 as being inserted towards the nose upper channel while FIG. 3 illustrates the nose catheter 200 as being fully inserted through the nose upper channel. It can effectively affect the temperature of the brain—especially cool it.

According to an embodiment of the invention the nose catheter can include three medical grade lumen tubes, wherein two lumens are adapted for liquid circulation and a third lumen is adapted for real time temperature measurement and comprises a thermocouple. The medical grade lumen tubes can be special extrude medical grade lumen tubes. The third lumen can include a Thermocouple that is located inside the lumen tube. Each of the two lumen tubes that are adapted for liquid circulation can include a designed tip that allows close loop circulation of desired temperature coming from the temperature control and fluid supply unit 100.

Figure 4:
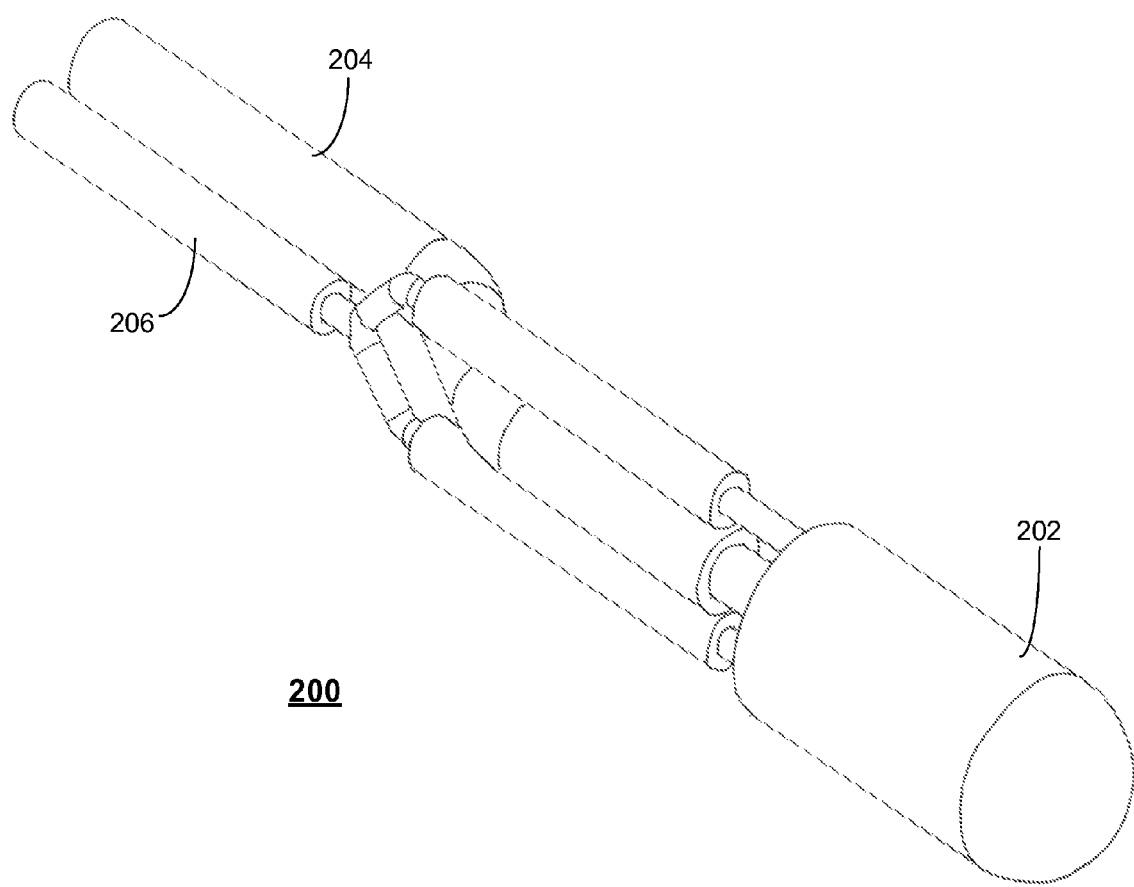
FIG. 4 illustrates a nose catheter according to an embodiment of the invention.

FIG. 4 illustrates nose catheter 200 as including tip such as stainless steel tip 202 that is connected to input and output tubes 204 and 206 that enable the closed loop circulation of fluid (referred to as first fluid) from temperature control and fluid supply unit 100, through tip 202 and towards temperature control and fluid supply unit 100. These tubes can be flexible, made of temperature conductive material.

Stainless steel tip 202 can be covered with silicon (or other interfacing material) which prevents direct contact with inside tissues of the patient. Tip 202 transports heat energy (for example low temperature heat energy) to local blood vessels into face parts and base of skull 402.

Nose catheter 200 is shaped in response to the nose anatomy and prevents direct impact to sensitive tissues. It enables a fast and efficient flow of liquid to keep nasal cavity at desired temperature while preventing constant pressure on Nasal walls.

Stomach Catheter

The nose catheter can be a non-invasive single use (disposable) catheter that is inserted through the mouth into the stomach of the patient.

The mid Esophagus lay in the center of chest, near the big vessels and the heart. The distal part of esophagus and the stomach are located in the abdominal cavity and close to the heart (only separated by a diaphragm) and to high blood flow organs such as the liver.

According to an embodiment of the invention the stomach catheter can include three medical grade lumen tubes, wherein two lumens are adapted for liquid circulation and a third lumen is adapted for real time temperature measurement and comprises a thermocouple. The medical grade lumen tubes can be special extrude medical grade lumen tubes. The third lumen can include a Thermocouple that is located inside the lumen tube. Each of the two lumen tubes that are adapted for liquid circulation can include a designed tip that allows close loop circulation of desired temperature coming from the temperature control and fluid supply unit 100.

Figure 6:
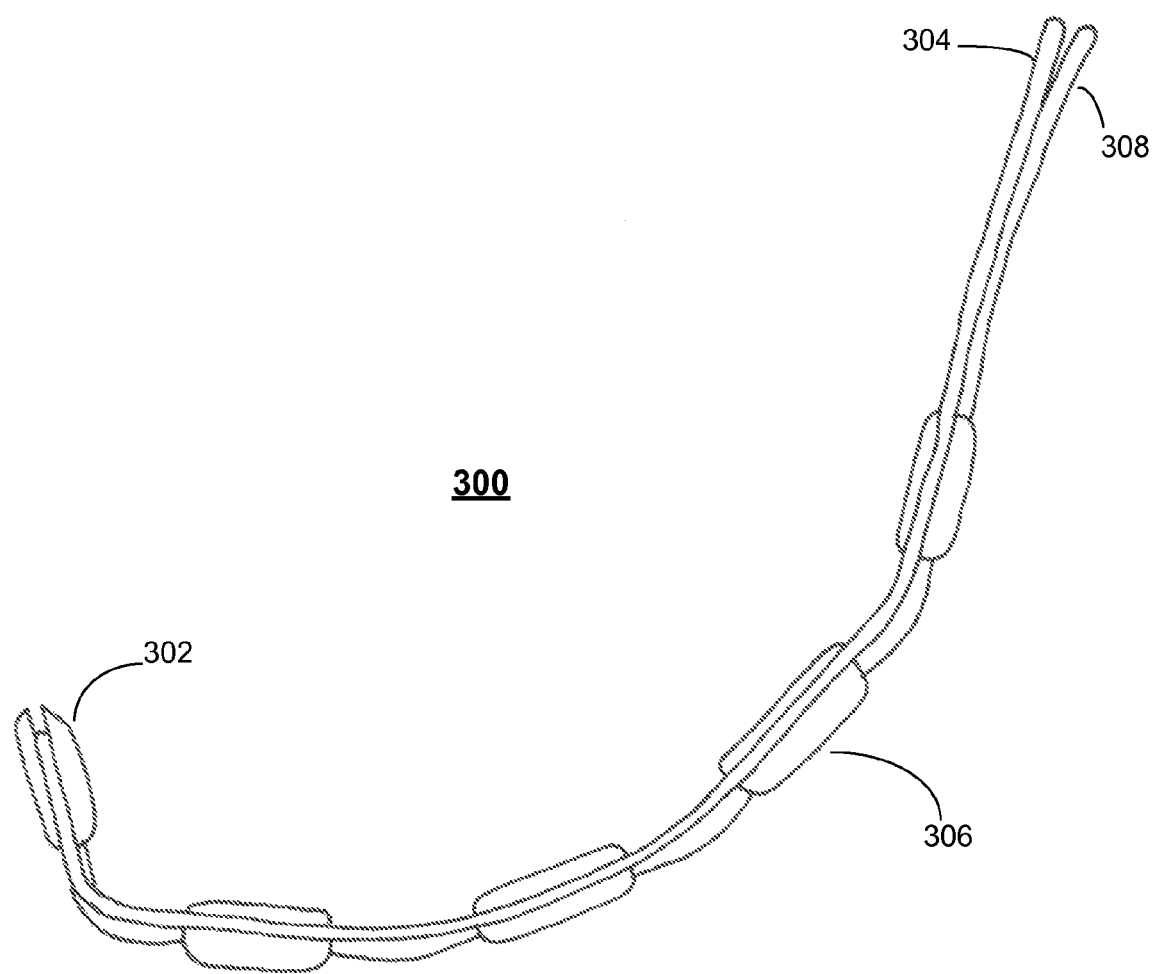
FIG. 6 is a stomach catheter according to an embodiment of the invention.

FIG. 1 illustrates stomach catheter 300 that is connected to temperature control and fluid supply unit 100. FIGS. 2 and 6 illustrates stomach catheter 300 as being inserted through the mouth towards the stomach of the patient.

Stomach catheter 300 can be inserted into the stomach. It receives fluid (referred to as a second fluid) from temperature control and fluid supply unit 100 via flexible tubes 304 and 308 (of FIG. 6). These tubes can be made of silicone.

Figure 5:
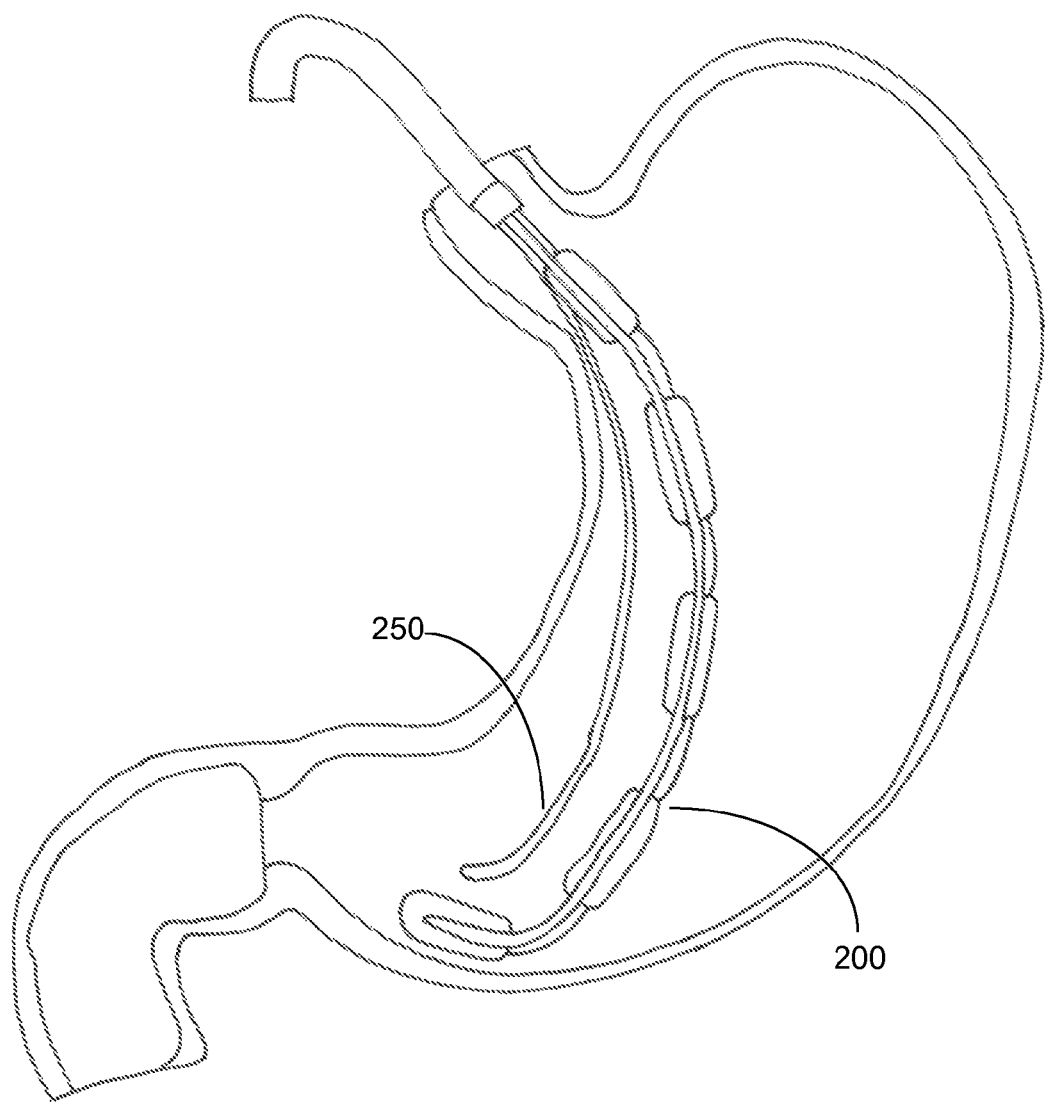
FIG. 5 is a cross sectional view of a stomach of the patient and a stomach catheter according to an embodiment of the invention.

Stomach catheter 300 can transport cooling or heating energy (via passage of the second fluid) to various organs such as the Heart and the Liver. In order to achieve a flexible form the stomach catheter is designed as joints (306 of FIG. 6) connected to two flexible silicon tubes (304 and 308) operating in a close loop unit. A regular Gastric tube (250 in FIG. 5) can be combined with stomach catheter 300 and also connected to temperature control and fluid supply unit 100. The gastric tube can include a temperature sensor.

Carotid Scarf

Figure 7:
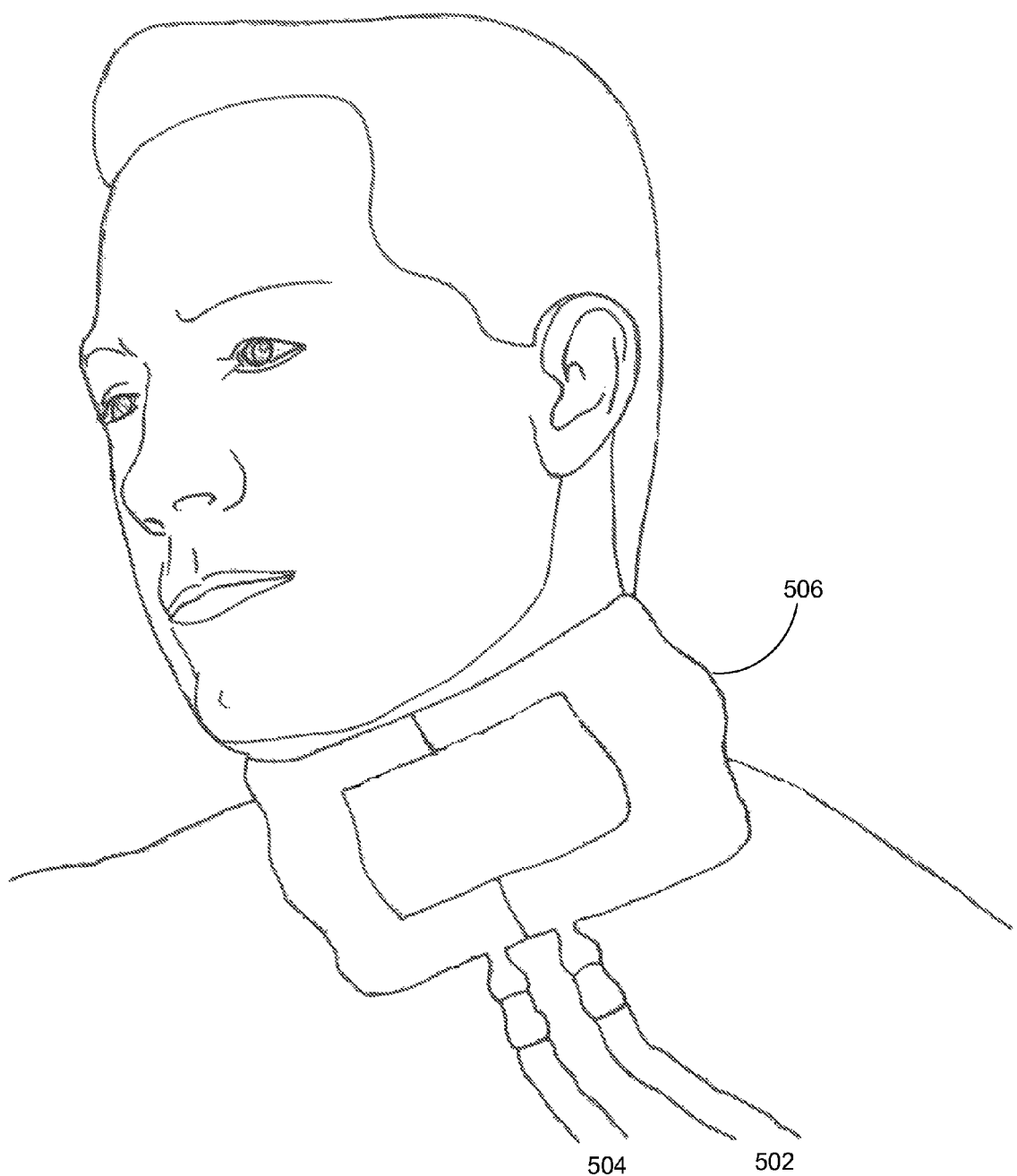
FIG. 7 illustrates a carotid scarf that is placed around the neck of a patient, according to an embodiment of the invention.

Carotid scarf (denoted 500 in FIG. 7) can be worn over the neck of the patient. It can be used instead of the nose catheter or in combination thereof. During operation, fluid (referred to as third fluid) from temperature control and fluid supply unit 100 flows through the carotid scarf and can affect the temperature of the patient.

Especially, the carotid scarf can cool the brain by cooling the main arteries that pass through the neck of the patient.

Carotid scarf 500 receives two tubes 502 and 504—one for providing fluid and the other for draining the fluid.

Carotid scarf can be made of flexible synthetic films and fabrics that form water passages (506 of FIG. 7) in order to keep in continual contact with the patient's skin surface without obstructing access to clinical procedures. The carotid scarf can have a soft layer in contact with patient's skin for comfort. The carotid scarf can be biocompatible and disposable, and can be available in various sizes, ranging from infants to adults.

The temperature of fluid that flows through carotid scarf 500 can be determined in view of a temperature of an organ of the patient.

Temperature Control and Fluid Supply Unit

FIGS. 8-11 illustrate various portions of temperature control and fluid supply unit 100 according to various embodiments of the invention. Temperature control and fluid supply unit 100 is illustrated in FIG. 1 as being connected to nose catheter 200 and to stomach catheter 300.

Temperature control and fluid supply unit 100, when connected to any element out of nose catheter 200, stomach catheter 300 and carotid scarf 500 forms a closed loop in which fluid can flow. While each of these elements (200, 300 and 500) and especially nose catheter 200, stomach catheter 300 are disposable, temperature control and fluid supply unit 100 can be re-sued as it does not contact and even enter the patient.

Temperature control and fluid supply unit 100 can independently control a temperature of fluid that flows through each element out of nose catheter 200, stomach catheter 300 and carotid scarf 500. These fluids are referred to as first, second and third fluids to illustrates the independent control of the temperature of each fluid. It is noted that this is not necessarily so and that according to another embodiment of the invention two or more of the mentioned above elements (200, 300, 500) can receive the same fluid that has the same temperature.

Temperature control and fluid supply unit 100 can determine the temperature of each fluid according to one or more parameters including but not limited to sensed temperature of an organ of a patient, medical history of the patient, temperature setting information indicative of desired fluid temperature per one or more parameters including patient age, patient weight, patient sex, patient status, and the like. The temperature setting information can include desired temperature changes over time.

Various prior art methods and systems can be applied for cooling or heating a fluid and for provided the cooled or heated fluid.

Conveniently, temperature control and fluid supply unit 100 is compact and can be easily carried or included in ambulances.

Figure 8:
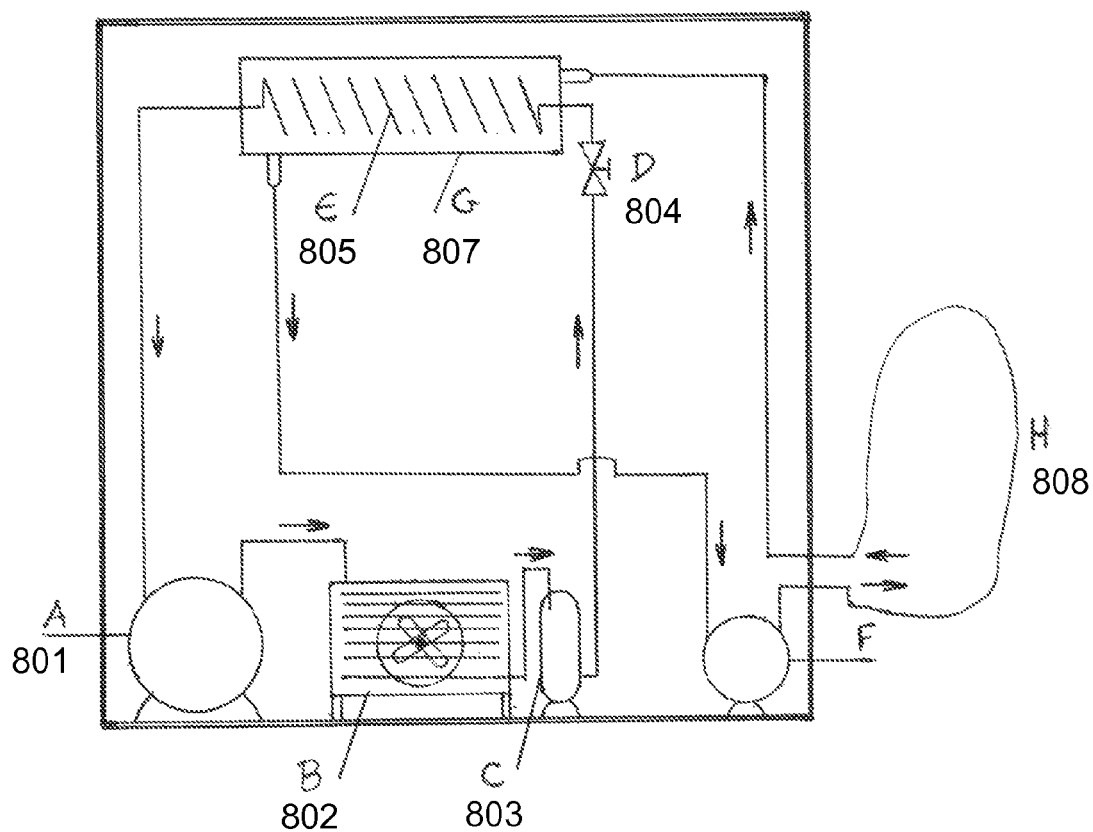
FIGS. 8-11 illustrate various portions of the temperature control and fluid supply unit according to various embodiments of the invention.

FIG. 8 illustrates a fluid refrigerating unit of temperature control and fluid supply unit 100 according to an embodiment of the invention.

Referring to FIG. 8, the fluid refrigerating unit includes: (A) Compressor 801, (B) Condenser 802, (C) Receiver 803, (D) Expansion valve 804, (E) Refrigerating coil 805, (F) Fluid pump 806, (G) Evaporator/Water tank 807, and (H) Closed loop water/fluid piping 808.

The compressor draws the refrigerant in the vapor phase from the evaporator or cooler and discharges it to the condenser at an increased temperature and pressure. Refrigerant reaches expansion valve as fluid and discharged into evaporator sprayed. There refrigerant evaporates and absorbs heat during the process from the cold body at the lowest temperature in the cycle.

The refrigerating process functions electrically and automatically by system's pre-adjustment for cold fluid supply at a stable temperature or by a manual instruction in view of changes in demands.

The pre-adjustment of the expansion valve and the thermostat (that can be regulated manually any time) keep the required temperatures from distortion.

Figure 9:
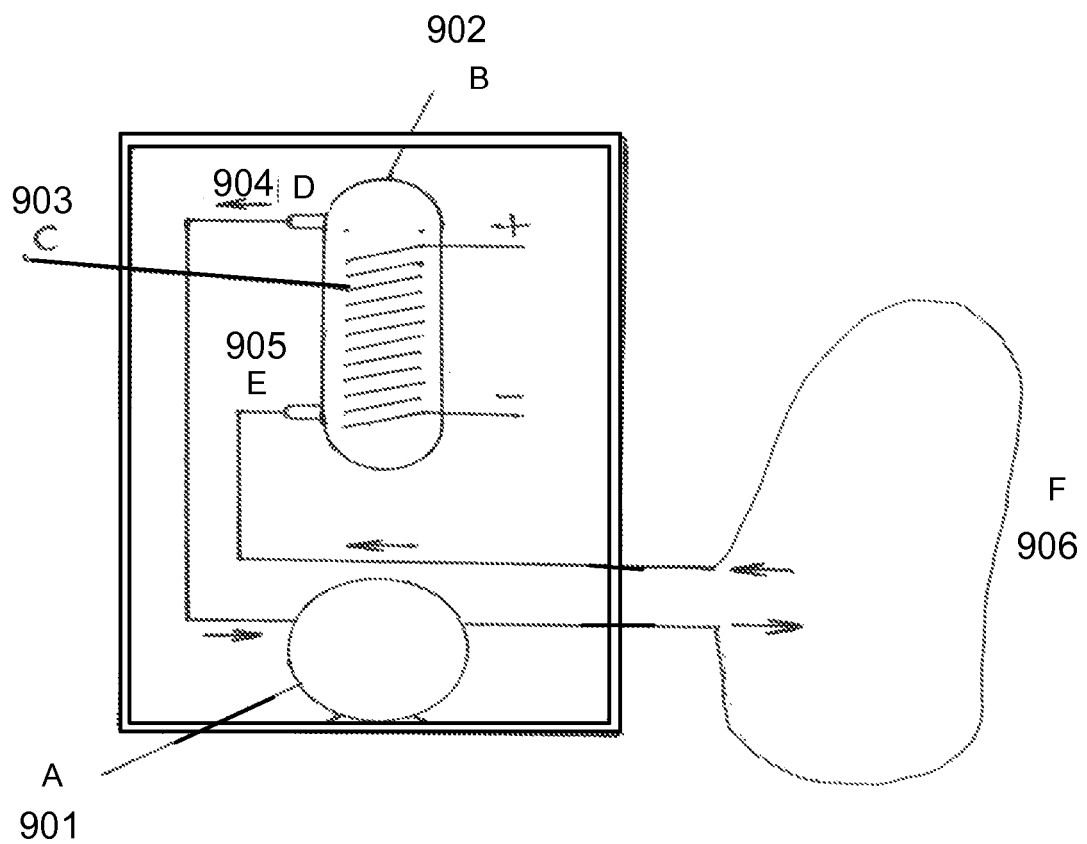

FIG. 9 illustrates a fluid heating unit of temperature control and fluid supply unit 100 according to an embodiment of the invention.

The fluid heating unit is close looped and contains several basic elements: (A) liquid pump 901, (B) a small water tank 902, (C) a high capacity electric element 903, (D) outlet of hot liquid 904, (E) inlet of returning liquid 905, and (F) closed loop water/fluid piping 906.

The small water tank contains the electric element and two openings.

The inlet and outlet of fluid—the fluid pump pumps hot fluid from the tank and discharges it by the closed loop piping to designated instruments and return in a loop into tank.

The heating process functions electrically and automatically by systems pre-adjustment for hot fluid supply at a stable temperature or by manual instruction in view of changes in demands. The pre-adjustment is by thermostat.

Referring to FIG. 9, the fluid heating unit includes: (i) Fluid pump pumps from upper part of fluid tank and discharges hot fluid by the closed loop piping to designated instruments and return in a loop into lower part of the tank. (ii) A small volume fluid tank (in order to decrease time of heating); (iii) An immersed electric element that heats fluid in tank in the demanded level of temperature and which is guarded by a thermostat; (iv) Outlet of hot fluid; (v) Inlet of returning fluid by loop piping; and (vi) Loop piping.

Figure 10:
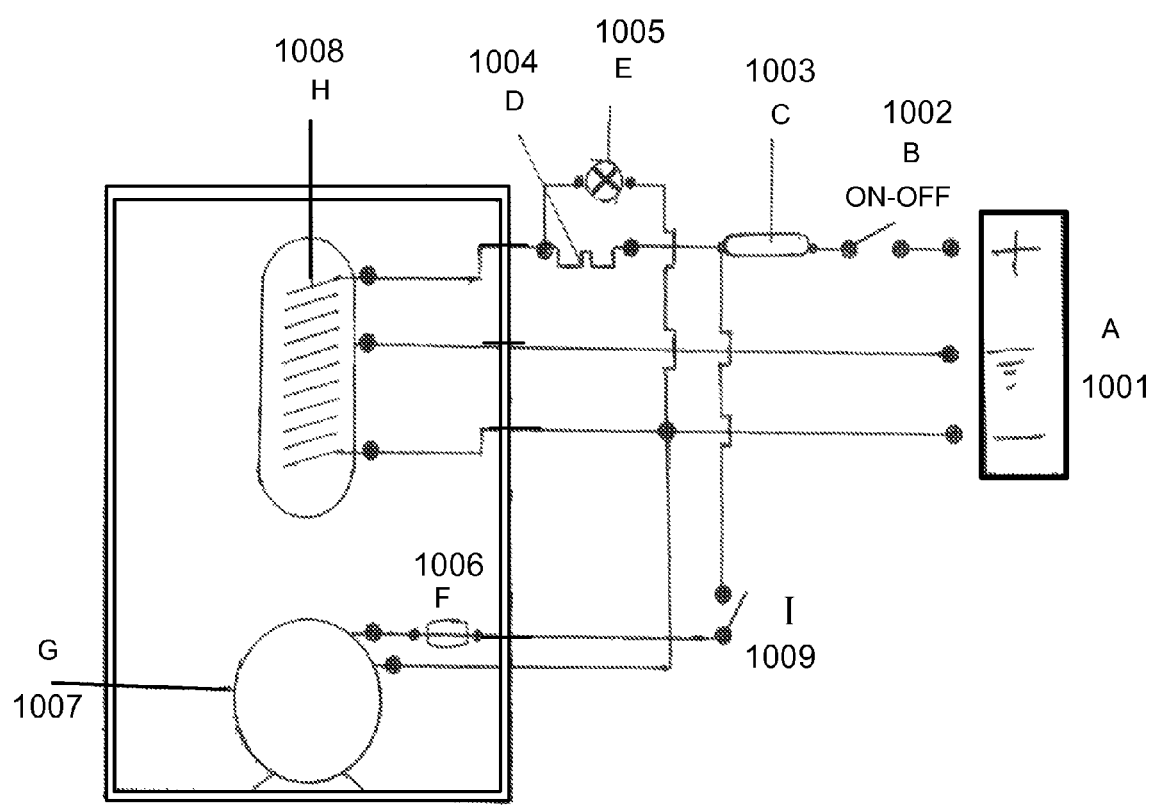

FIG. 10 provides an electrical scheme of the fluid heating unit.

It includes: Direct power supply 12 v (A) 1001, on/off main switch 1002, Fuse 1003, Thermostat 1004, Light emitting diode 1005, Flow switch 1006, Pump 1007, Heater element 1008, and discharging fluid switch to closed loop piping.

By operating the main switch (B) 1002 the system is under current. The fluid in tank is cold, so thermostat's probe (D) 1004 enables current reach the heater element (H) 1008 and led (E) 1005 lights up. While fluid reaches the right temperature level, thermostat's probe (D) 1004 causes current cut down and heating stops. Likewise led (E) 1005 goes out.

When hot fluid supply is required a switch 1009 must be pressed (I) and by that, flow switch (F) 1006 causes the pump (G) 1007 operate and discharge fluid.

As long as the switch (I) 1009 will be pressed, hot fluid will keep flowing into closed loop piping.

Figure 11:
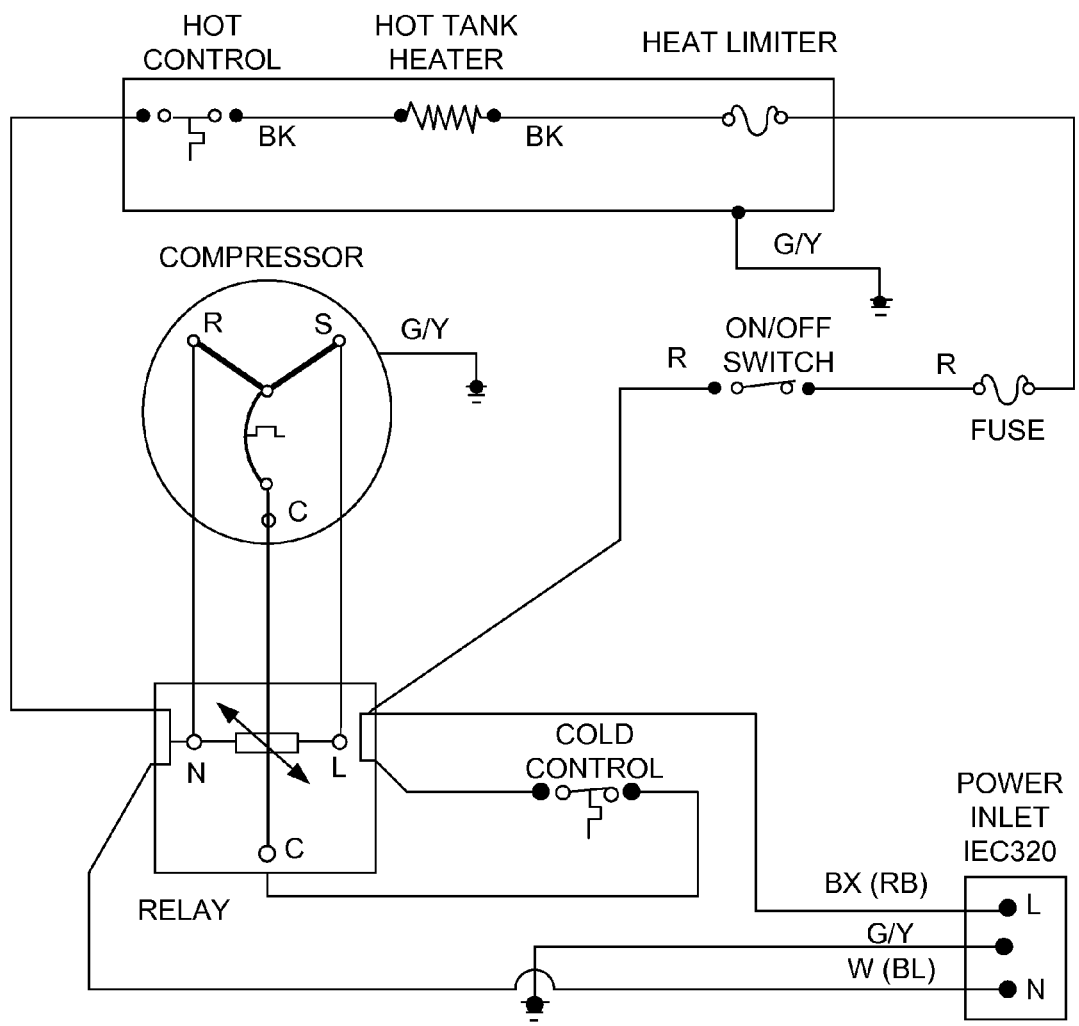

FIG. 11 illustrates an electrical schema of the system. It illustrates some of the elements of the previous figures. For example, it illustrates a three phase compressor, that can be fed by a relay that is controller by a cold circuit switch. It also illustrates a hot control switch that can selectively connect or disconnect hot tank heater (represented by a resistor) to the supply power. A heat limiter and fuse protect the elements of the system from over currents. In addition an ON/OFF switch can turn the system on or off.

Figure 12:
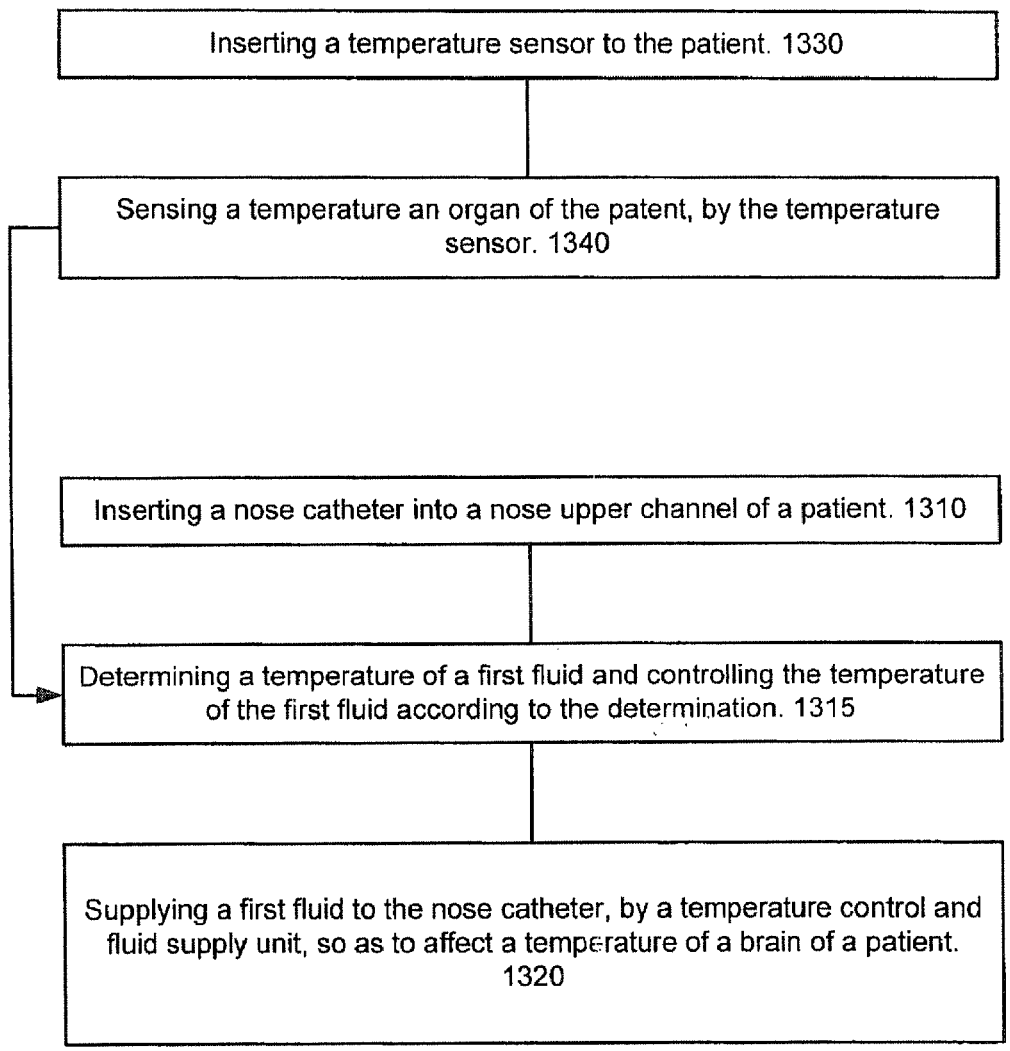
FIG. 12 illustrates a method for affecting a temperature of a client according to an embodiment of the invention.

FIG. 12 illustrates method 1300 for affecting a temperature of a patient, according to an embodiment of the invention.

Method 1300 starts by stage 1310 of inserting a nose catheter into a nose upper channel of a patient. Stage 1310 can include inserting a nose catheter that includes a stainless steel tip. Stage 1310 can be preceded by coating the tip with silicon or other barrier.

Stage 1310 is followed by stage 1315 of determining a temperature of a first fluid and controlling the temperature of the first fluid according to the determination.

Stage 1315 is followed by stage 1320 of supplying a first fluid to the nose catheter, by a temperature control and fluid supply unit, so as to affect a temperature of a brain of a patient. Stage 1320 can include supplying the first fluid to the nose catheter through an inlet and draining the fluid through the outlet.

Stages 1315 and 1320 can be executed during a long period of time. The temperature can be dynamically changed over time.

Conveniently, stage 1320 includes supplying the first fluid to the nose catheter so as to cool the brain of the patient.

Method 1300 can also includes stage 1330 of inserting a temperature sensor to the patient. Stage 1330 is followed by stage 1340 of sensing a temperature an organ of the patent, by the temperature sensor. Stage 1340 can be followed by stage 1315 wherein the determining of the temperature of the first fluid is responsive to temperature sensed by the temperature sensor. It is noted that method 1300 can include inserting more than a single temperature sensor and determining the temperature of the first fluid in response to multiple sensed temperatures.

Figure 13:
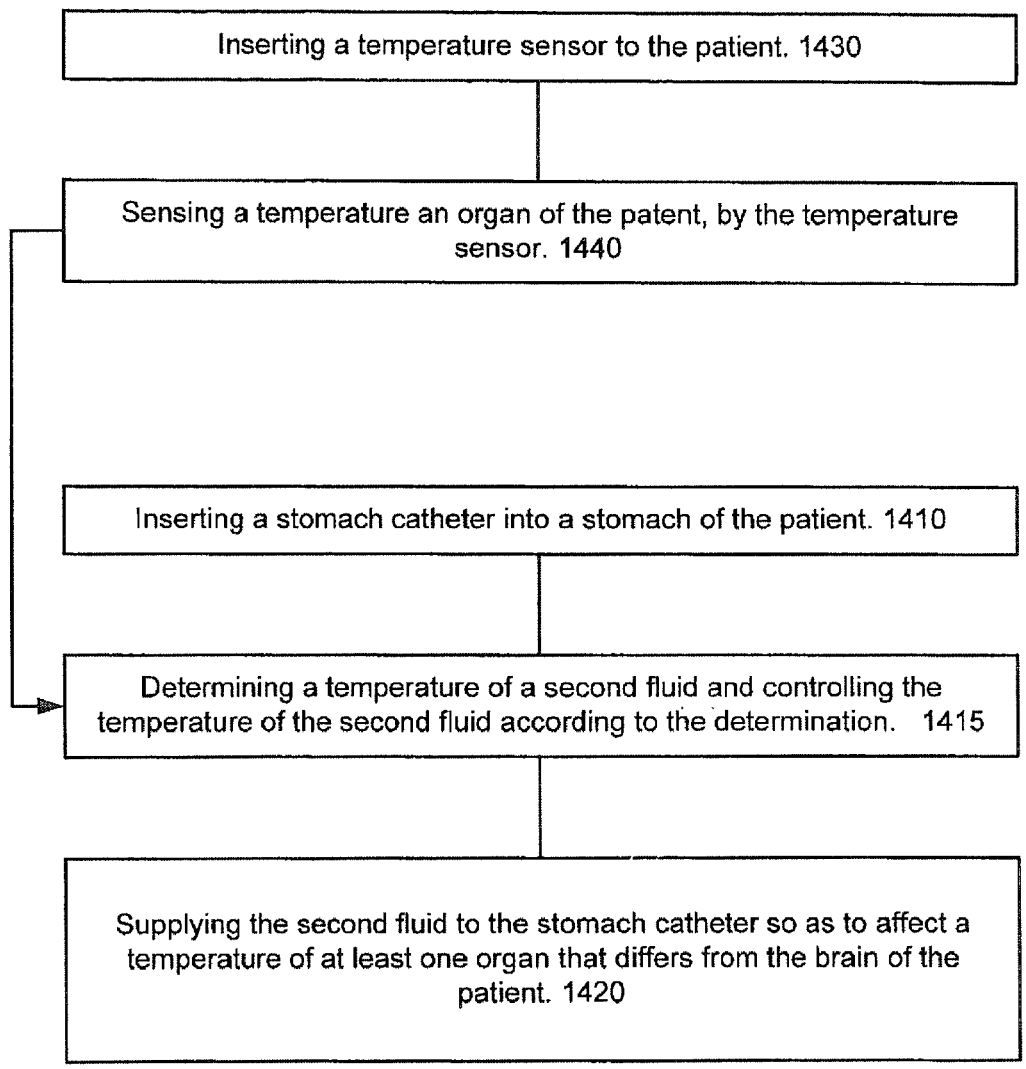
FIG. 13 illustrates a method for affecting a temperature of a client according to an embodiment of the invention.

FIG. 13 illustrates method 1400 for affecting a temperature of a patient, according to an embodiment of the invention.

Method 1300 starts by stages 1310 and 1410.

Stage 1310 is followed by stage 1315. Stage 1315 is followed by stage 1320.

Stage 1410 includes inserting a stomach catheter into a stomach of the patient.

Stage 1410 is followed by stage 1415 of determining a temperature of a second fluid and controlling the temperature of the second fluid according to the determination.

Stage 1415 is followed by stage 1420 of supplying the second fluid to the stomach catheter so as to affect a temperature of at least one organ that differs from the brain of the patient. This organ can be the liver, the heart, the stomach and the like.

It is noted that one or more temperature sensors can sense the temperature of these one or more other organs and that stage 1415 can be responsive to the sensed temperature—as illustrated by stage 1430 and 1440.

Stages 1315 and 1415 can facilitate controlling temperatures of the first and second fluids so that during at least one period of time, the temperature of the first fluid differs from the temperature of the second fluid.

Stages 1315 and 1415 can facilitate controlling temperatures of the first and second fluids so that during at least one other period of time, the temperature of the first fluid substantially equals the temperature of the second fluid.

Stages 1315 and 1415 can facilitate controlling temperatures of the first and second fluids so that during a first period of time, the stomach catheter and the nasal catheter cool organs of the patient and during a second period of time that followed the first period of time the nasal catheter cools the brain of the patient while the stomach catheter warms at least one other organ of the patient.

Figure 14:
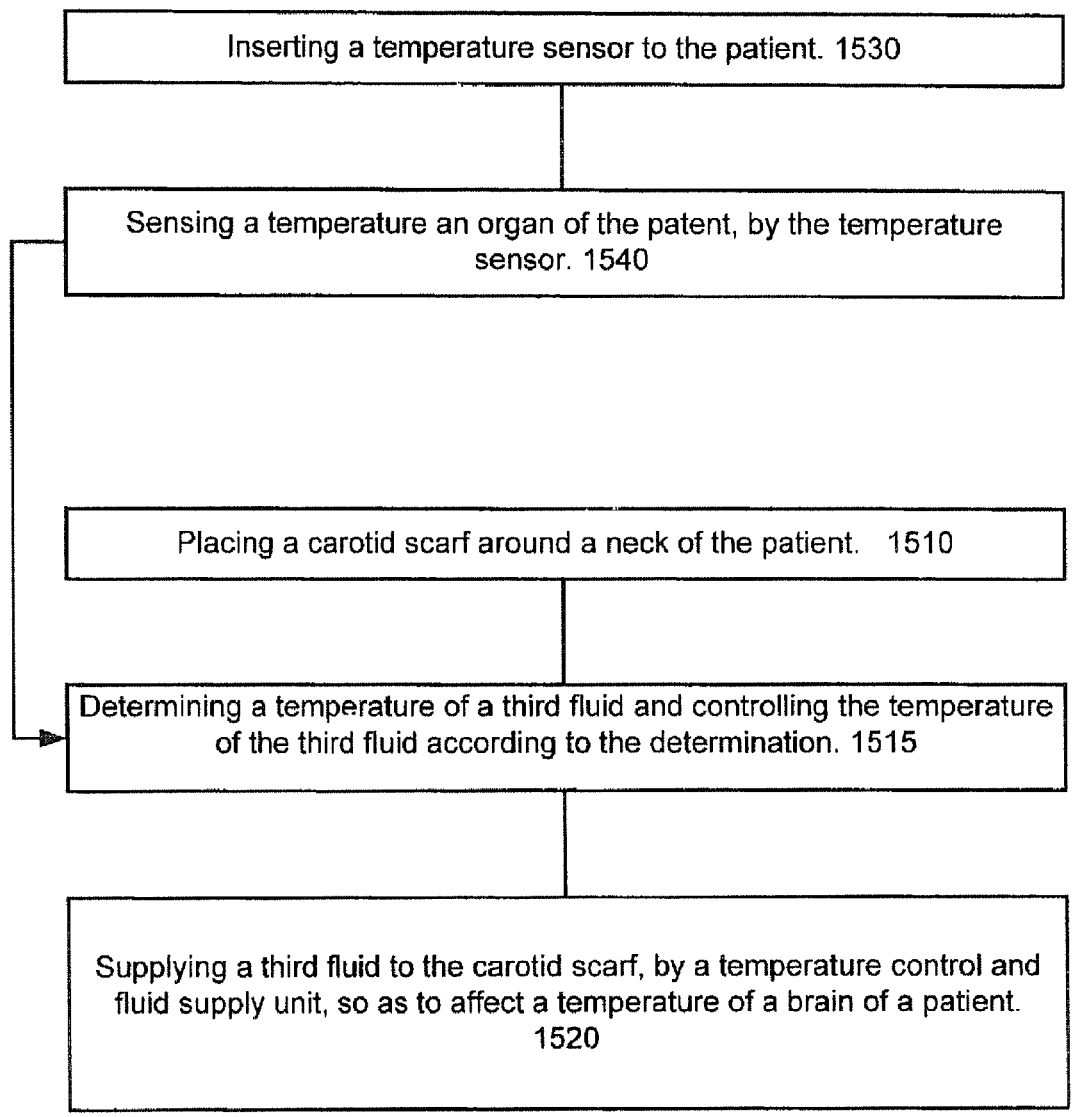
FIG. 14 illustrates a method for affecting a temperature of a client according to an embodiment of the invention.

FIG. 14 illustrates method 1500 for affecting a temperature of a patient, according to an embodiment of the invention.

Method 1500 starts by stage 1510 of placing a carotid scarf around a neck of the patient.

Stage 1510 is followed by stage 1515 of determining a temperature of a third fluid and controlling the temperature of the third fluid according to the determination.

Stage 1515 is followed by stage 1520 of supplying a third fluid to the carotid scarf, by a temperature control and fluid supply unit, so as to affect a temperature of a brain of a patient.

Method 1500 can also includes stage3 1530 and 1540 that are analogues to stage 1330 and 1340.

Conveniently, method 1500 also includes at least one sequence of stages of method 1300 or 1400.

It is noted that any combination of the above method methods or stages can be applied. For example, a method can include utilizing a combination of nose catheter, carotid scarf and stomach catheter. Yet for another example, only a combination of carotid scarf and stomach catheter can be utilized. Yet for a further example, a head helmet can be used in addition to any method.

However, other modifications, variations, and alternatives are also possible. The specifications and drawings are, accordingly, to be regarded in an illustrative rather than in a restrictive sense.

The word 'comprising' does not exclude the presence of other elements or steps then those listed in a claim.

Furthermore, the terms "a" or "an," as used herein, are defined as one or more than one. Also, the use of introductory phrases such as "at least one" and "one or more" in the claims should not be construed to imply that the introduction of another claim element by the indefinite articles "a" or "an" limits any particular claim containing such introduced claim element to inventions containing only one such element, even when the same claim includes the introductory phrases "one or more" or "at least one" and indefinite articles such as "a" or "an." The same holds true for the use of definite articles. Unless stated otherwise, terms such as "first" and "second" are used to arbitrarily distinguish between the elements such terms describe. Thus, these terms are not necessarily intended to indicate temporal or other prioritization of such elements. The mere fact that certain measures are recited in mutually different claims does not indicate that a combination of these measures cannot be used to advantage.

I claim:

1. A system for affecting a temperature of a patient, the system comprises: a nasal catheter that is adapted to be inserted into a nose upper channel and to receive a first fluid; a temperature control and fluid supply unit that is adapted to supply the first fluid and control a temperature of the first fluid so as to affect a temperature of a brain of a patient when the nasal catheter is inserted into the nose upper channel of a patient and receives the first fluid; and a stomach catheter that is adapted to be inserted into a stomach of the patient and to receive a second fluid; wherein the temperature control and fluid supply unit is further adapted to supply the second fluid and control a temperature of the second fluid so as to affect a temperature of at least one organ that differs from the brain of the patient when the stomach catheter is inserted into the nose upper channel of the patient and receives the second fluid; wherein the temperature control and fluid supply unit is adapted to control temperatures of the first and second fluids so that during a first period of time, the stomach catheter and the nasal catheter cool organs of the patient and during a second period of time that followed the first period of time the nasal catheter cools the brain of the patient while the stomach catheter warms at least one other organ of the patient.

2. A system for affecting a temperature of a patient, the system comprises: a nasal catheter that is adapted to be inserted into a nose upper channel and to receive a first fluid; a temperature control and fluid supply unit that is adapted to supply the first fluid and control a temperature of the first fluid so as to affect a temperature of a brain of a patient when the nasal catheter is inserted into the nose upper channel of a patient and receives the first fluid; and a carotid scarf that is adapted to be surround a neck of the patient and to receive a third fluid; and wherein the temperature control and fluid supply unit is further adapted to supply the third fluid and control a temperature of a second fluid so as to affect a temperature the brain of the patient when the stomach catheter is inserted into the nose upper channel of the patient and receives the second fluid.

3. The system according to claim 2, further comprising a stomach catheter that is adapted to be inserted into a stomach of the patient and to receive the second fluid; and
   wherein the temperature control and fluid supply unit is further adapted to supply the second fluid and control a temperature of the second fluid so as to affect a temperature of at least one organ that differs from the brain of the patient when the stomach catheter is inserted into the nose upper channel of the patient and receives the second fluid.

4. A method for affecting a temperature of a patient, the method comprises: inserting a nasal catheter into a nose upper channel of a patient; supplying a first fluid to the nasal catheter, by a temperature control and fluid supply unit, so as to affect a temperature of a brain of a patient; inserting a stomach catheter into a stomach of the patient; and supplying a second fluid to the stomach catheter so as to affect a temperature of at least one organ that differs from the brain of the patient; and controlling temperatures of the first and second fluids so that during a first period of time, the stomach catheter and the nasal catheter cool organs of the patient and during a second period of time that followed the first period of time the nasal catheter cools the brain of the patient while the stomach catheter warms at least one other organ of the patient.

5. A method for affecting a temperature of a patient, the method comprises: inserting a nasal catheter into a nose upper channel of a patient; supplying a first fluid to the nasal catheter, by a temperature control and fluid supply unit, so as to affect a temperature of a brain of a patient; placing a carotid scarf around a neck of the patient; and supplying a third fluid to the carotid scarf, by a temperature control and fluid supply unit, so as to affect a temperature of a brain of a patient.

6. A method for affecting a temperature of a patient, the method comprises: inserting a nasal catheter into a nose upper channel of a patient; supplying a first fluid to the nasal catheter, by a temperature control and fluid supply unit, so as to affect a temperature of a brain of a patient; and wherein the nasal catheter that comprises three medical grade lumen tubes, wherein two lumens are adapted for liquid circulation and the third lumen is adapted for real time temperature measurement and comprises a thermocouple.

7. A system for affecting a temperature of a patient, the system comprises: a nasal catheter that is adapted to be inserted into a nose upper channel and to receive a first fluid; a temperature control and fluid supply unit that is adapted to supply the first fluid and control a temperature of the first fluid so as to affect a temperature of a brain of a patient when the nasal catheter is inserted into the nose upper channel of a patient and receives the first fluid; wherein the nasal catheter comprises three medical grade lumen tubes, wherein two lumens are adapted for liquid circulation and the third lumen is adapted for real time temperature.

* * * * *